United States Patent [19]

Noack et al.

[11] Patent Number: 5,292,940
[45] Date of Patent: Mar. 8, 1994

[54] PROCESS FOR THE PREPARATION OF ALKALI METAL SALTS OF ETHER-CARBOXYLIC ACIDS

[75] Inventors: Wolf-Eckart Noack, Essen; Gerd Goebel, Koeln; Holger Tesmann, Duesseldorf; Franz-Josef Carduck, Haan; Harald Liebs, Leverkusen; Willi Wuest, Ratingen, all of Fed. Rep. of Germany

[73] Assignee: Henkel Kommanditgesellschaft auf Aktien, Duesseldorf, Fed. Rep. of Germany

[21] Appl. No.: 73,919

[22] Filed: Jun. 8, 1993

Related U.S. Application Data

[63] Continuation of Ser. No. 836,325, Apr. 28, 1992, abandoned.

[30] Foreign Application Priority Data

Sep. 1, 1989 [DE] Fed. Rep. of Germany ....... 3929063

[51] Int. Cl.$^5$ ............................................. C07C 51/16
[52] U.S. Cl. ................................................... 562/538
[58] Field of Search .............................. 562/538, 537

[56] References Cited

U.S. PATENT DOCUMENTS

| | | | |
|---|---|---|---|
| 3,342,858 | 9/1967 | Fuhrmann et al. | 260/531 |
| 4,214,101 | 7/1980 | Miya et al. | 562/421 |
| 4,348,509 | 9/1982 | Sanders et al. | 562/538 |
| 4,607,121 | 8/1986 | Faggian et al. | 562/537 |
| 5,162,579 | 11/1992 | Fried | 562/538 X |
| 5,175,360 | 12/1992 | Fried | 562/538 |

FOREIGN PATENT DOCUMENTS

| | | |
|---|---|---|
| 0018681 | 2/1983 | European Pat. Off. . |
| 0039111 | 8/1983 | European Pat. Off. . |
| 0073545 | 1/1985 | European Pat. Off. . |
| 0304763 | 3/1989 | European Pat. Off. . |
| 2936123 | 4/1981 | Fed. Rep. of Germany . |
| 3135946 | 3/1983 | Fed. Rep. of Germany . |
| 2816127 | 9/1983 | Fed. Rep. of Germany . |
| 3446561 | 7/1985 | Fed. Rep. of Germany . |
| 2152050 | 7/1985 | United Kingdom . |

OTHER PUBLICATIONS

Ullmann, Enzyklopädie der technischen Chemie, 4th edition, vol. 3, 1973, pp. 390–392.
Ullmann, Enzyklopädie der technischen Chemie, 4th edition, vol. 2, 1972, pp. 529, 533/534.
Ullmann, Enzyklopädie der technischen Chemie, 5th edition, vol. B3, 1988, pp. 4–82/83.
JP/Abstract, 1149752 (1989).

Primary Examiner—Arthur C. Prescott
Attorney, Agent, or Firm—Ernest G. Szoke; Wayne C. Jaeschke; John E. Drach

[57] ABSTRACT

A process for the preparation of alkali metal salts of ether-carboxylic acids by oxidation of etheralcohols in an aqueous phase with oxygen or gases containing oxygen at elevated temperatures in the presence of alkali metal hydroxides and noble metal catalysts, in which an aqueous solution, containing an alkali metal hydroxide solution, of the ether-alcohols is brought into contact in a thin layer on a solid carrier or in the form of fine particles with oxygen or the gases containing oxygen as a continuous phase, the concentration of the ether-alcohols in the aqueous phase being in the range from 0.1 to 15% by weight, based on the total weight of the aqueous phase, enables aqueous solutions of the alkali metal salts of the ether-carboxylic acids in high concentrations to be prepared.

15 Claims, 1 Drawing Sheet

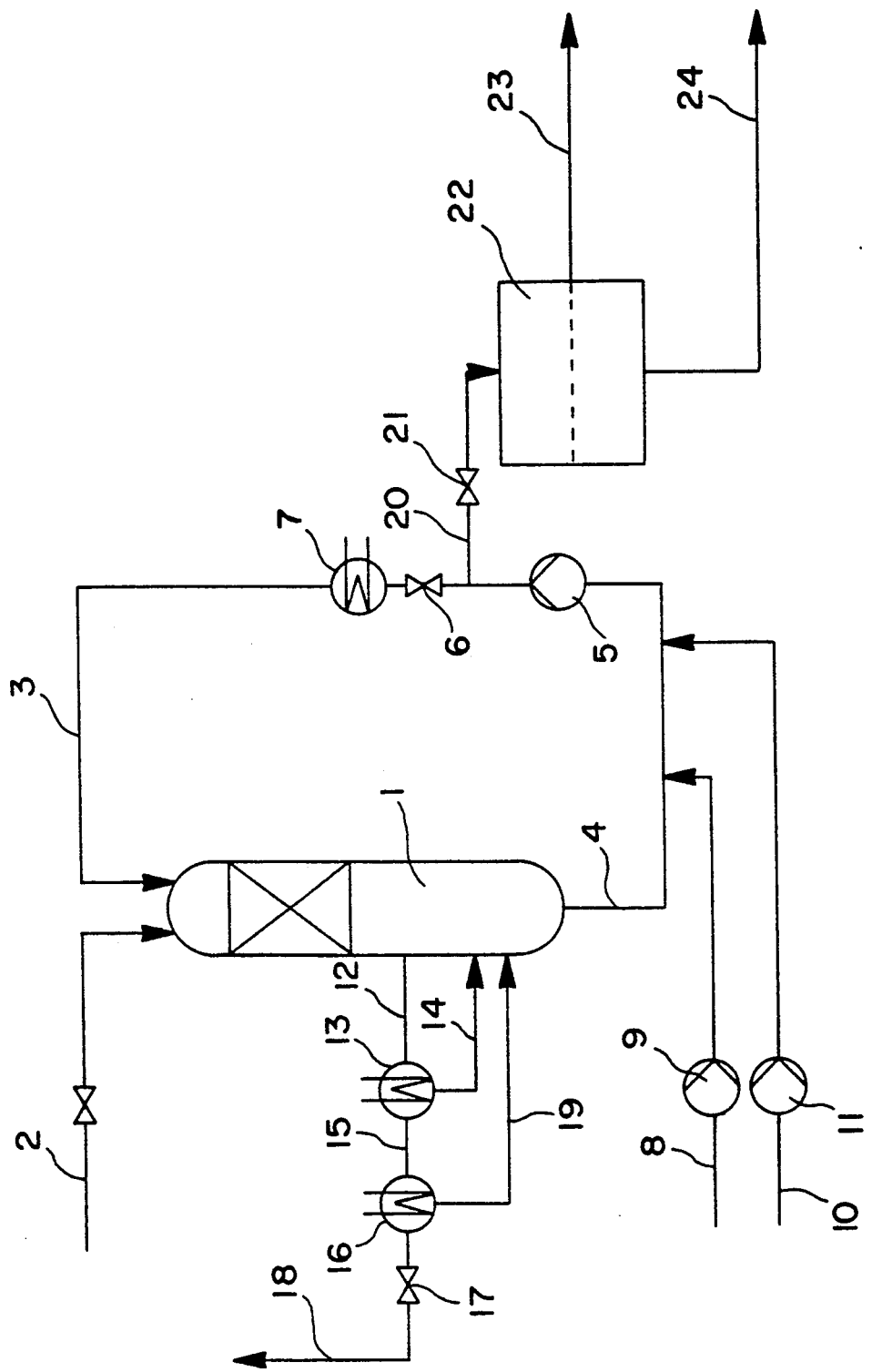

PROCESS FOR THE PREPARATION OF ALKALI METAL SALTS OF ETHER-CARBOXYLIC ACIDS

This application is a continuation of application Ser. No. 07/836,325 filed Apr. 28, 1992, now abandoned.

BACKGROUND OF THE INVENTION

1. Field of the Invention

The invention relates to a process for the preparation of alkali metal salts of ether-carboxylic acids of the general formula I $$R-(OC_mH_{2m})_n-O-CH_2COOM \quad (I)$$

in which
- R denotes an alkyl group having 1 to 22 carbon atoms, an aryl group or an aralkyl group,
- m denotes the number 2 and/or 3,
- n denotes a number in the range from 0 to 20 and
- M denotes an alkali metal from the group formed by lithium, sodium and potassium, by oxidation of ether-alcohols of the general formula II $$R-(OC_mH_{2m})_n-OCH_2CH_2OH \quad (II)$$

in which
R, m and n are as defined above,
in the aqueous phase with oxygen or gases containing oxygen at elevated temperatures in the presence of alkali metal hydroxides and noble metal catalysts.

2. Statement of Related Art

Alkali metal salts of ether-carboxylic acids are compounds which have intersecting surface-active properties and are employed in the form of their aqueous solutions, for example in cosmetics formulations.

It is known that alkali metal salts of ether-carboxylic acids of the general formula I can be prepared by catalytic oxidation of the corresponding ether-alcohols of the general formula II, compare EP-B-0,039,111, EP-B-0,018,681, EP-B-0,073,545, US-C-3,342,858, DE-C-2,816,127, DE-A-3,135,946, DE-A-2,936,123 and DE-A-3,446,561.

However, only dilute solutions of the alkali metal salts of the ether-carboxylic acids can be prepared by the known catalytic processes. In particular, if oxygen or a gas containing oxygen is passed into a relatively highly concentrated solution of the ether-alcohols in water in the presence of the catalysts, the viscosity of the reaction mixture increases greatly as the conversion increases, passes through a maximum at about 30% conversion (about 30% of sodium salt of the ether-carboxylic acid and about 70% of ether-alcohol) and then drops greatly again as the conversion becomes higher; compare DE-C-2,816,127. The rate of reaction becomes so slow during this procedure, because the mass transfer is impeded by the viscosity, that the process is uneconomical since the reaction time is then too long; in the extreme case, the reaction here can even stop completely. Low concentrations of an organic substance (that is to say total weight of ether-alcohol and sodium salt of the ether-carboxylic acid) are therefore used in the known processes in order to avoid a high increase in the viscosity. However, this requires subsequent concentration.

It is indeed possible for the dilute aqueous solutions of the alkali metal salts of the ether-carboxylic acids obtained after the oxidation to be concentrated by removing some of the water contained in the solutions by distillation or by acidifying the solutions with strong acids, for example with sulfuric acid, liberating the ether-carboxylic acid and precipitating it, isolating the ether-carboxylic acid and preparing concentrated aqueous solutions after renewed conversion into the alkali metal salts. However, these processes have the following disadvantages:

1. Aqueous solutions of alkali metal salts of ethercarboxylic acids foam greatly during removal of the water by distillation. The profitability of the process is moreover greatly reduced by the energy required for removal of water by distillation.

2. During precipitation of the ether-carboxylic acids with acids, the aqueous phase which remains is polluted by a high salt load, residual ether-carboxylic acids and unreacted ether-alcohol; its disposal is uneconomical. Renewed conversion of the ether-carboxylic acids into their alkali metal salts also leads to an additional increase in the costs of the reaction product.

An additional hindrance occurs in particular if air is used as the oxidizing agent. In this case, the oxidation procedure is made difficult by the foam formed as a result of the surface-active properties of the starting substances and end products. The foam issues from the reactor with the waste gas and must be recycled from there back into the reactor after its destruction. The rate of foam formation is always high if air is dispersed in the solution, as is the case, for example, in agitator vessel reactors or bubble column reactors. In agitator vessel reactors in particular, the reaction solution can be converted into a foam-like state by the stirring action, so that mass transfer of the oxygen is prevented and the reaction is inhibited; compare DE-C-2,816,127.

The invention relates to a process for the preparation of alkali metals salts of ether-carboxylic acids of the abovementioned type, in which the above-mentioned disadvantages in respect of the increase in viscosity and the foaming of the reaction mixture are avoided and highly concentrated aqueous solutions of alkali metal salts of the ether-carboxylic acids, for example having a concentration of 20 to 50% by weight, based on the total weight of the solution, can be obtained.

According to the invention, this object is achieved by bringing an aqueous solution, containing an alkali metal hydroxide solution, of the ether-alcohols in a thin layer on a solid support or in the form of fine particles or droplets into contact with oxygen or the gases containing oxygen as the continuous phase, the concentration of the ether-alcohols in the aqueous phase being in the range from at least 0.1, in particular from 0.5 to 15% by weight, based on the total weight of the aqueous phase. Below the stated range the rate of reaction is generally too low so that the concentration should fall below this range only towards the end of the reaction, when the addition of ether-alcohol has ended.

Alkali metal salts of ether-carboxylic acids of the general formula (I) in which the group R can be a straight-chain or branched alkyl group having 1 to 22 carbon atoms can be prepared by the process according to the invention; typical examples of such alkyl groups are methyl, ethyl, propyl, butyl, pentyl, hexyl, heptyl, octyl, nonyl, decyl, dodecyl, tetradecyl, hexadecyl, octadecyl, eicosyl and docosyl. The process according to the invention is particularly suitable for the preparation of alkali metal salts of ether-carboxylic acids in which the radical R is derived from $C_{12}$–$C_{18}$-fatty alcohols, or industrial mixtures thereof, obtainable from animal and/or vegetable fats and oils. The group R can also be an aryl radical, for example a phenyl group, or an aralkyl radical, for example a phenylalkylene group having 1 to 3 carbon atoms in the alkylene radical.

If $n>0$, the compound of the general formula II is an addition product of ethylene oxide or ethylene oxide and propylene oxide on alcohols of the formula ROH, it being possible, in the case of the ethylene oxide/propylene oxide adducts of the formula II, for the propyleneglycol radicals to be in random or block distribution in the alkoxylate chain, but a terminal ethyleneglycol radical always being present. Addition products of ethylene oxide on alcohols of the formula II are preferred in the context of the invention, so that $m=2$ is a preferred meaning for the compounds of the formulae I and II.

The increase in viscosity which occurs at higher concentrations of ether-alcohols is avoided if, according to the invention, the reaction is started with only a low ether-alcohol concentration at the beginning and ether-alcohol is metered into the reaction solution continuously or in portions as the reaction progresses further, and in particular at a rate such that the concentration of the ether-alcohols in the reaction mixture does not exceed the value of 15% by weight.

The abovementioned problem of foaming is avoided or considerably reduced by the reaction solution being present in the form of thin layers on a solid support or in the form of fine particles in a continuous phase of oxygen or gases containing oxygen.

According to an advantageous embodiment of the process according to the invention, the oxidation is carried out at a temperature in the range from 40 to 130° C., in particular 60 to 85° C. The rate of reaction is too low below the stated range. Although the reaction can also be carried out above the stated range, this gives only an insignificant increase in the rate of reaction.

According to another advantageous embodiment of the process according to the invention, the oxidation is carried out under an oxygen partial pressure of 0.1 to 5 bar. With oxygen-containing gases in particular, foaming is suppressed more and more as the system pressure increases and the effective gas throughput thus decreases. The rate of reaction furthermore increases under certain circumstances as the oxygen partial pressure increases.

According to another advantageous embodiment of the invention, the oxidation is carried out with air. This is another considerable advantage over the processes known from the prior art, in which oxygen is in general used in order to prevent the nitrogen content of air as the oxidizing agent promoting undesirable foaming, and in order to carry out the reaction without a waste gas.

Useful catalysts for use in the process according to the invention are the noble metal catalysts known from the abovementioned prior art, in particular those based on platinum or palladium. Palladium catalysts, for example palladium-un-charcoal, have proved to be particularly suitable for the process according to the invention. The catalyst is preferably introduced into the process in the form of a suspension in the aqueous solution of the ether-alcohols. However, it is also possible for the catalyst to be located on a solid support material, over which the aqueous solution of the ether-alcohols is passed. Possible support materials for this purpose are, for example, active charcoal, graphite, kieselguhr, silica gel, spinels, aluminum oxide or ceramic materials. The catalysts can furthermore also contain combinations of a plurality of noble metals instead of one noble metal, for example mixtures of Pd and Pt, and moreover suitable activators, such as lead, bismuth or cadmium, in the form of their metals or their compounds, including combinations thereof. Suitable catalysts are described in the abovementioned literature and in U.S. Pat. No. 4,607,121.

According to another advantageous embodiment of the process according to the invention, the catalyst is employed in the form of a suspension in a concentration of 0.2 to 3% by weight, based on the total weight of the suspension containing the ether-alcohols and water.

The process according to the invention is in general carried out at pH values of at least 8. Particularly advantageous pH values are at least 9, in particular in the range from 9 to 11. Surprisingly, it has been found that, in contrast to the doctrine of U.S. Pat. No.4,607,121, in spite of these high pH values neither dissolving of the catalyst nor oxidative chain degradation or by-product formation occurs when air is used as the oxidizing agent; the end product of the process according to the invention is Pd-free and the catalyst can be reused after washing with hot water and treatment with hydrogen.

According to another advantageous embodiment of the invention, the oxidation of the ether-alcohols is carried out in a reactor in which the oxygen or the gases containing oxygen and the aqueous phase containing the ether-alcohol, alkali metal hydroxide solution and if appropriate the catalyst are introduced at the top of the reactor, the reaction mixture containing ether-carboxylic acid salts, unreacted ether-alcohol and if appropriate the catalyst is removed at the bottom part of the reactor and the reaction mixture is recycled to the upper part of the reactor for renewed oxidation of as yet unreacted ether-alcohol. It is preferable here for alkali metal hydroxide solution, for maintaining the pH of at least 9, in particular 9 to 11, and ether-alcohol, for maintaining the ether-alcohol concentration of at least 0.1, in particular 0.5 to 15% by weight in the reaction mixture, to be added continuously to the reaction mixture removed at the lower part of the reactor before recycling to the upper part.

According to another advantageous embodiment of the invention, packed columns of the usual construction, such as are described, for example, in Ullmann, Enzyklopadie der Technischen Chemie, 4th edition, volume 3, pages 390 to 392 (1973), Verlag Chemie, Weinheim, as parallel flap packed columns, are used for carrying out the process.

The packings to be employed in the packed columns advantageously have a high intermediate volume so that the gas speed and the rate of foaming does not become too high. Typical examples of suitable packings are known from Ullmanns Enzyklopädie der technischen Chemie, 4th edition, volume 2, page 529 (1972) and 5th edition, volume B3, pages 4-82 to 4-83 (1988); the use of Pall rings, Novalox saddles, Berl saddles, Intralox saddles and Interpack bodies is particularly preferred. Ordered packings such as are described in volume 2 of the 4th edition of the abovementioned encyclopedia, pages 533–534, for example of the Sulzer packing type, can furthermore also be employed. Finally, it is also possible to employ bulk catalysts or catalyst fixed beds instead of bulk packing. Ordered catalyst packings, for example in honeycomb form, can also be employed.

According to another advantageous embodiment of the invention, the reaction mixture removed at the lower end of the column is recycled, after the pH and the ether-alcohol concentration has been adjusted, to the upper part of the column for renewed reaction until a concentration of the ether-carboxylic acid salt of 20 to 50% by weight, based on the total weight of the solution, is reached and the ether-alcohol metered in has reacted.

The invention is illustrated in more detail below with the aid of the drawing and a preferred exemplary embodiment.

BRIEF DESCRIPTION OF DRAWINGS

The drawing shows a schematic representation of an installation for carrying out the process according to the invention.

The installation comprises a packed column 1 which is provided at its upper end with a feedline for oxygen or gases containing oxygen, in particular air. A line 3 serves to feed in the water/ether-alcohol mixture, containing the suspended catalyst if appropriate. A line 4 is located at the lower end of the packed column for removal of the oxidized reaction mixture; the reaction mixture can be recycled to the top of the packed column via a circulating pump 5, a valve 6, which is open during the reaction and closed only during the filtration discussed below, and a heat exchanger 7 and via line 3. Aqueous sodium hydroxide solution is fed in via line 8 and a metering pump 9, and the ether-alcohol to be oxidized is fed in via line 10 and a metering pump 11. The waste air flowing out of the packed column 1 is removed laterally via line 12 and passed to a waste gas heater 13. In this, the foam formed, for example during incorrect operation of the installation, and entrained with the waste air can be destroyed and recycled to the reactor as a liquid via line 14. The waste air which has been freed from the foam is fed via line 15 to a cooler 16 and is removed from the system via a valve 17 and line 18; any entrained droplets of liquid or condensate obtained are likewise recycled to the reactor via a line 19. The aqueous suspension containing the end product is removed via a line 20 and a valve 21 and fed to a filter unit 22 where the aqueous solution of the process products and the suspended catalyst are separated, these each being removed via lines 23 and 24 respectively. The catalyst is introduced at a point not shown in line 4.

The installation shown in FIG. 1 is operated as follows:

In the packed reactor flushed with nitrogen, the suspension of the pulverulent noble metal catalyst in water is recycled from the bottom of the reactor to its top by means of the circulating pump 5. When the solution has been heated to the reaction temperature by the heat exchanger 7 in the solvent circulation, a small amount of ether-alcohol and sodium hydroxide solution is metered in the form of an aqueous solution into the circulating suspension by means of the metering pumps 9, 10. The nitrogen is then displaced by oxygen or a gas containing oxygen and immediately after the desired pressure has been reached, the gas throughput required for the oxidation and the metering in of sodium hydroxide solution and alcohol via the metering pumps 9 and 11 are adjusted.

During the reaction, which is detectable by an oxygen uptake, alcohol and aqueous sodium hydroxide solution are metered in continuously. The metering rate is adjusted or varied and matched to the rate of reaction. so that a small amount of ether-alcohol which has not yet reacted and therefore a low viscosity is ensured in the solution throughout the entire course of the reaction When the required amounts of ether-alcohol and sodium hydroxide solution have been metered in, the metering is stopped; the reaction is then continued until oxygen uptake decreases significantly.

When the reaction has ended, the gas feed is interrupted and the catalyst is separated off from the solution by filtration.

EXAMPLE 1

A customary packed column of internal diameter 50 mm and height of the packing of 1000 mm was used for this exemplary embodiment; the column was charged with packing of the type Interpack 15/40.

The feed material was a commercially available fatty alcohol ethoxylate (addition product of about 4 mol of ethylene oxide on an industrial fatty alcohol of chain length $C_{12}$–$C_{14}$, molecular weight: 369). A palladium catalyst containing 5% of palladium-on-charcoal (Degussa), which had been reduced with hydrogen before use in the form of an aqueous suspension, was used as the catalyst.

The installation was initially charged with a suspension of, based on the dry substance, 35 g of catalyst in 2400 g of demineralized water. To start the reaction, 30 g of ether-alcohol (about 1.2% by weight) and 3.3 g of NaOH (as 25% strength sodium hydroxide solution) were metered into the installation. The particular content of free ether-alcohol was determined mathematically from the amount of oxygen taken up by the reaction solution by the period up to each point in time of the reaction and the amount of ether-alcohol metered in by then.

In detail, the process parameters were as follows:
System pressure: 1.9 bar absolute
Suspension temperature: 75° C.
Air throughput (reactor outlet): 30 Nl/hour
Solution circulation: 170 l/hour
Metering rate of ether-alcohol: about 140 g/hour (0.379 gmol)
Metering rate of NaOH (calculated as 100% strength NaOH): 15.2 g/hour (0.379 gmol/hour)
Total amount of ether-alcohol metered in: 720 g (1.95 gmol)
Total amount of NaOH metered in (as 100% strength NaOH): 78.0 g (1.95 gmol)
Average or maximum content of ether-alcohol which has not yet reacted: 3 and 4% by weight respectively
Duration of the reaction: 6.3 hours
Conversion (determined mathematically from the $O_2$ uptake and the NaOH consumption): about 97%.

When the reaction has ended and the catalyst has been removed by filtration, an approximately 23% strength solution of the sodium salt of the ether-carboxylic acid formed, based on the total weight of the solution, was obtained with a pale yellow color. NMR analysis of the process product showed an average degree of ethoxylation which was lower than that of the ether-alcohol by one unit. Atomic spectroscopy analysis of the filtrate on palladium showed a content of <1 ppm.

The experiment was performed seven times using the same catalyst without losses in activity being detectable. Before each use, the catalyst was washed with hot water, suspended in water and reduced with $H_2$ at room temperature.

EXAMPLE 2

An addition product of on average 5 mol of ethyleneoxide on 1 mol of the industrial fatty alcohol described in Example 1, of chain length $C_{12}-C_{14}$, was oxidized by a process analogous to that of Example 1. After a reaction time of 6.7 hours, a 23.5% strength solution of the sodium salt of the corresponding ether-carboxylic acid was obtained in a conversion of about 97%, calculated from the oxygen consumption. An addition product of on average 9 mol of ethylene oxide on 1 mol of an industrial fatty alcohol of chain length $C_{12}-C_{18}$ was oxidized in the same manner. After a reaction time of 6.2 hours, a 19.5% strength solution of the sodium salt of the corresponding ether-carboxylic acid was obtained at a conversion, calculated from the oxygen consumption, of about 105%.

In deviation from the procedure of the exemplary embodiment explained above, it is also possible to use starting concentrations other than 1.2% by weight of ether-alcohol. Thus, for example, the reaction can also be started without initial addition of ether-alcohol, that is to say the ether-alcohol is metered in only at the start of the introduction of air. However, this procedure can lead to a premature discontinuation of the reaction and must therefore be regarded as unstable. Higher initial concentrations, for example of 7% by weight of ether-alcohol, are also possible, but offer no advantages in respect of the duration of the reaction in the case of the ether-alcohol employed in the present exemplary embodiment.

It has proved advantageous for an adequate rate of reaction to choose the NaOH metering so that at each point in time the acid formed up until that point has been bonded completely; at this equivalence point, the solution has a pH of about 9. However, a significantly higher rate of reaction is obtained if the total amount of NaOH metered in at each point in time is equivalent to the total amount of ether-alcohol metered in, that is to say at pH values of more than 9, for example of 10 to 11. No oxidative chain degradation on the ethoxylate groups and no dissolving of the catalyst were to be found even at these higher pH values.

Finally, it is also possible for the entire amount of NaOH to be initially introduced from the beginning; however, this is not an advantage in respect of the duration of the reaction compared with the reaction procedure described above in the exemplary embodiment.

We claim:

1. A process for the manufacture of alkali metal salts of an ether-carboxylic acid of the general formula I $$R-(OC_mH_{2m})_n-O-CH_2COOM \quad (I)$$

in which R stands for an alkyl group having from 1 to 22 carbon atoms, an aryl group of an aralkyl group, m stands for the number 2 or 3, n stands for a number in the range of from 0 to 20 and M stands for an alkali metal selected from the group consisting of lithium, sodium and potassium, which comprises oxidizing an ether-alcohol of the general formula II $$R-(OC_mH_{2m})_n-O-CH_2CH_2OH \quad (II)$$

in which R, m and n are defined as above, in the aqueous phase with oxygen or an oxygen containing gas at elevated temperatures in the presence of an alkali metal hydroxide and a precious metal catalyst wherein an aqueous, alkali lye containing solution of ether alcohols in a thin layer on a solid carrier or in the form of micrometric particles at a pH value of at least 9 is brought into contact with oxygen or an oxygen containing gas as a continuous phase, wherein the concentration of the ether alcohols in the aqueous phase is in the range from at least 0.5 to 15 weight-%-related to the total weight of the aqueous phase.

2. The process as claimed in claim 1, wherein the process is carried out at a temperature in the range from 40 to 130° C.

3. The process as claimed in claim 1, wherein the process is carried out under an oxygen partial pressure in the range from 0.1 to 5.

4. The process as claimed in claim 1 wherein the oxygen containing gas is air.

5. The process as claimed in claim 1 wherein the catalyst is suspended in the aqueous solution of the ether-alcohol.

6. The process as claimed in claim 1 wherein the catalyst is employed in a concentration of 0.2 to 3% by weight, based on the total weight of the suspension containing the ether-alcohol and 7. The process as claimed in claim 1 wherein the process is carried out at a pH of 9 to 11.

8. The process as claimed in claim 1, wherein the process is carried out in a reactor in which the oxygen or an oxygen containing gas and the aqueous phase containing the ether carboxylic acid salt, unreacted ether-alcohol and the catalyst is removed at the bottom part of the reactor and the reaction mixture is recycled to the upper part of the reactor for renewed oxidation of the unreacted ether-alcohol.

9. The process as claimed in claim 8, wherein alkali metal hydroxide solution, to maintain the pH of at least 9, and ether-alcohol, to maintain the ether-alcohol concentration of at least 0.1, in the reaction mixture, are added continuously to the reaction mixture removed at the lower part of the reactor before recycling to the upper part.

10. The process as claimed in claim 8, wherein a packed column is used.

11. The process as claimed in claim 8, wherein the reaction mixture is recycled to the reactor until a concentration of the ether-carboxylic acid salt of 20 to 50% by weight, based on the total weight of the solution, is reached and the ether-alcohol metered in has reacted.

12. The process as claimed in claim 2 wherein the temperature range is from 60 to 85° C.

13. The process as claimed in claim 3 wherein the oxygen partial pressure range is from 0.2 to 3 bar.

14. The process as claimed in claim 7 wherein the pH range is from 9 to 11.

15. The process as claimed in claim 9 wherein the pH range is maintained between 9 and 11 and the ether-alcohol concentration is maintained in the range of 0.5 to 15% by weight.

* * * * *

UNITED STATES PATENT AND TRADEMARK OFFICE
CERTIFICATE OF CORRECTION

PATENT NO. : 5,292,940
DATED : March 8, 1994
INVENTOR(S) : Noack et. al.

It is certified that error appears in the above-indentified patent and that said Letters Patent is hereby corrected as shown below:

In claim 6, column 8, line 27, after "and", insert:
-- water --.

Signed and Sealed this

Eighteenth Day of April, 1995

Attest:

BRUCE LEHMAN

*Commissioner of Patents and Trademarks*

*Attesting Officer*